United States Patent
Lv

(10) Patent No.: US 8,511,149 B2
(45) Date of Patent: Aug. 20, 2013

(54) DETECTION DEVICE FOR FLUID SAMPLE

(75) Inventor: Xinlong Lv, Yuhuan (CN)

(73) Assignees: Hangzhou D2 Technology Co., Ltd, Hangzhou, Zhejiang Province (CN); Xinlong Lv, Yuhuan, Zhejiang Province (CN); Jielin Dai, Hangzhou, Zhejiang Province (CN)

( * ) Notice: Subject to any disclaimer, the term of this patent is extended or adjusted under 35 U.S.C. 154(b) by 271 days.

(21) Appl. No.: 13/003,152

(22) PCT Filed: Jul. 2, 2009

(86) PCT No.: PCT/CN2009/000748
§ 371 (c)(1),
(2), (4) Date: Jan. 7, 2011

(87) PCT Pub. No.: WO2010/003310
PCT Pub. Date: Jan. 14, 2010

(65) Prior Publication Data
US 2011/0107824 A1    May 12, 2011

(30) Foreign Application Priority Data

Jul. 7, 2008 (CN) .................. 2008 2 0121124 U
Jul. 23, 2008 (CN) .................. 2008 1 0063222

(51) Int. Cl.
*G01N 1/10* (2006.01)
(52) U.S. Cl.
USPC .................. 73/64.56; 73/863.31; 73/863.33; 73/863
(58) Field of Classification Search
USPC ........................................ 73/64.56
See application file for complete search history.

(56) References Cited

U.S. PATENT DOCUMENTS

| 5,351,563 A | * | 10/1994 | Karpf et al. ................. 73/864.84 |
| 5,579,933 A | * | 12/1996 | Hofmann ....................... 215/220 |
| 6,786,106 B2 | | 9/2004 | Alley |
| 7,144,496 B2 | * | 12/2006 | Meserol et al. ............... 205/792 |
| 2006/0029517 A1 | | 2/2006 | Hartselle |
| 2009/0031790 A1 | * | 2/2009 | Guo et al. ..................... 73/64.56 |

FOREIGN PATENT DOCUMENTS

| CN | 1181695 A | 5/1998 |
| CN | 1377300 A | 10/2002 |
| CN | 2724003 Y | 9/2005 |
| CN | 2763795 Y | 3/2006 |
| CN | 1834622 A | 9/2006 |
| CN | 1842299 A | 10/2006 |
| CN | 20120157 Y | 3/2009 |
| CN | 201229339 Y | 4/2009 |

OTHER PUBLICATIONS

English Translation of CN 1834622.*

* cited by examiner

*Primary Examiner* — Hezron E Williams
*Assistant Examiner* — Alexander Mercado
(74) *Attorney, Agent, or Firm* — Jacobson Holman PLLC; Jiwen Chen

(57) ABSTRACT

This invention provides a device for detecting an analyte in a liquid sample, comprising a cup body (7), a lid (1) and a base (15), wherein, said the cup body (7) comprises a liquid storage chamber (9) and a test strip groove locating in one side of liquid storage chamber, the storage chamber (9) and the test strip groove communicates each other through a small hole in the bottom of liquid storage chamber, the test strip groove is configured with a test strip plate, said lid being able to seal the opening of the cup tightly, said opening of cup being directly connected with the liquid storage chamber.

14 Claims, 10 Drawing Sheets

DETECTION DEVICE FOR FLUID SAMPLE

This is a U.S. national stage application of PCT Application No. PCT/CN/2009/000748 under 35 U.S.C. 371, filed Jul. 2, 2009 and published in Chinese, claiming the priority benefit of Chinese Application No. 200820121124.5, filed Jul. 7, 2008 and Chinese Application No. 200810063222.2, filed Jul. 23, 2008 in China.

FIELD OF THE INVENTION

The present invention relates to a device for detecting analytes in fluid samples, particularly to a device for detecting liquid samples easily and sanitarily.

DESCRIPTION OF THE PRIOR ART

In the fields of medicine, criminal investigation and competitive sports, detection of liquid, particularly urine, is very common, since the compositions in the urine usually represent various symptoms of human body and helps to judge the compositions of food that people ate. Therefore, detection of urine is helpful to medical treatment, criminal investigation and fair competitive sports. Common detection methods of liquid sample use chromatographic analysis to detect the presence of specific "marks" in the liquid. The marks are different colors represented on the test strips. According to different colors, one can judge the types and quantities of the compositions contained in the liquid. In practice, operators usually collect a specific quantity of liquid (mainly urine) with an open container, and then insert test strips in a liquid, and finally read the test results after the color of test strip becomes stable. This method has the following main problems:

1. Generally, an open container is not carefully sealed, so that samples tend to be affected by the environment and become deteriorate, thus impairing the accuracy of the test.
2. In the course of storing with such open containers, samples are easily substituted or diluted by some ill-intentioned persons particularly in competitive sports so as to impair the fairness.
3. People conducting the tests tend to directly contact liquid sample and be polluted to impair their hygiene.
4. It is very hard to detect a liquid sample of a small quantity.

In order to solve the above-mentioned problems, people have made many trials. Chinese Utility Model CN3000077.7 disclosed a device to detect liquid samples. It contains a clear box and a kind of test strips. Test strips are tiled and fixed on the inner top of clear box lid that is movably and hermetically coupled to the box. During operation, such a device can store liquid sample in itself. When beginning to detect, an operator tilts the box to allow liquid to contact with the test strips, and judge the masses and quantity contained in the liquid by color change of test strips. Such a device can achieve an effect of hygiene and convenience. However, since test strips and liquid are stored in the same closed space for a long time, test strips tend to pollute samples and affect the accuracy of detection. Moreover, this invention has not taken irreversible design of sealing into consideration. In case of less amount of a liquid sample, detection is hard to be fulfilled. After retrieval of relevant products, no solution has been found for all aforesaid problems simultaneously.

China Patent CN1834622A disclosed a device and method for detecting analytes in fluid samples. The detecting device contains the opening through which a liquid sample is introduced into a first chamber. The first chamber communicates with a second chamber through a hole. Detecting elements are installed in the second chamber. The detecting device also contains a third chamber communicating with the second chamber through a passage and containing a mobile element. The mobile element has a first position and a second position. The mobile element divides the third chamber into a first zone and a second zone. The first zone is provided with a first vent. The mobile element is hermetically coupled to the wall surface of the third chamber to prevent the air in the first zone and in the second zone from mutually communicating. Such a detecting device is provided with three cavities of which the third chamber provides dynamics for the whole detection. The piston movement inside the third chamber results in the enlargement of the third chamber and then introduces in the air in the second chamber, causing the whole air pressures in the second and third cavities to drop, thus form a difference of air pressure between the first chamber and the second chamber. The balanced state of liquid sample kept by tension is thus broken, so that the liquid sample flows from the first chamber to the second chamber. After flowing through the test strips in the second chamber, the sample is absorbed by the test strips and results will be represented on the test strips. Although by only pressing the piston can the detecting device complete the whole operation, yet the structure of the device is complicated, especially for the piston control in the third chamber. The piston assembly contains piston chamber, piston, vent, passage communicating the first and second cavities, seal ring and so on. The piston chamber is part of baffle plate inside cup body, which increases difficulties for processing. The piston must be installed in piston chamber before installing piston seat, which makes assembly rather troublesome.

Since the third chamber transfers dynamics by air, an adequate negative pressure must be produced. However, in the detecting device, the first chamber forms a sealed space under the role of sealing element of lid body and the seal ring in the upper part of piston. The piston is still dropping before forming the sealed space, increasing the pressure difference between the second and the third cavities; meanwhile the air intake of the first chamber is rapidly decreased. Once the piston moves downwards, not only the volume of the third chamber will be increased, but also the volume of the first chamber will be increased. Since the decrease of air intake of the first chamber results in the air pressure of the first chamber being less than the atmosphere, the first chamber is in the state of negative pressure compared to the atmosphere. Meanwhile, the downward movement of the piston results in the air pressure of the second and third cavities to drop, so that the second and third cavities are also in the state of negative pressure. However their air pressures are less than the air pressure of the first chamber. Thus, there exists a pressure difference between the first chamber and the latter two cavities. Since the state of negative pressure of the first chamber cause the pressure difference to be unable to reach the maximum value, the liquid filling amount to the second chamber is reduced. The reduction of liquid filling amount weakens the reliability of testing result and tends to cause the misjudgment of operators.

SUMMARY OF THE INVENTION

The present invention aims at solving the following problems in prior art: inadequate seal, allowable reopening after sealing, easily contamination to operators, and difficulties in tests for samples of less quantity by providing a device for detecting analytes in fluid samples with a simple structure, convenient processing and assembly, low cost and offering adequate pressure difference. In order to solve another technical problem, the present invention provides a device for detecting analytes in fluid samples that can start detection at any time after collecting liquid samples, ensure technicians to supervise the process of detecting samples, and guarantee the safety and fairness of each sample detection.

The above-mentioned technical problems are solved by the following technical proposals in the present invention. The device of detecting liquid sample comprises a cup body, a lid and a base, wherein said cup body comprises a liquid storage chamber and a test strip groove locating in one side of the liquid storage chamber and communicating with the liquid storage chamber through a small hole. The small hole locates in the bottom of liquid storage chamber. The test strip groove is configured to match with a test strip plate. The lid can seal the opening of the cup tightly. The opening of the cup is directly connected with the liquid storage chamber. Since the lid seals the opening of the cup tightly, the liquid in the liquid storage chamber can only enter into the test strip groove in a small amount through the small hole, while the liquid in test strip groove is not easy to enter into the liquid storage chamber. This can avoid the pollution to the liquid in the liquid storage chamber and affect test result. Such a structure that needs not to open the liquid storage chamber to take liquid has the advantages of cleanness, sanitation and safety.

Preferably, the test strip groove and base jointly form a sealed chamber. The test strip groove is comprised of a test strip plate slot and a liquid discharge groove. The test strip plate slot matches with the test strip plate. The liquid discharge groove locates under the lower portion of a liquid storage chamber and directly communicates with the test strip plate slot and communicates with liquid storage chamber through the hole in its bottom. Said lid is provided with a piston seat. A plunger element contains a connecting end and a working end. Said connecting end of the plunger element matches with the piston seat in the lid, and said working end of the plunger element matches with the inner wall of opening of cup. In the course of tightening the lid onto the opening of the cup, the plunger element is moved downwards. The pressure in the liquid storage chamber increases and presses a quantity of liquid into test strip groove through the hole.

Preferably, the side wall of the test strip plate slot is provided with an air filtering hole communicating with the outer atmosphere. The air filtering hole is covered by an air filtering film. When the liquid does not reach the height of the air filtering hole, the liquid can flow from the liquid storage chamber into the test strip groove continuously due to the principle of communicating vessel. When the liquid level in test strip groove is higher than the air filtering hole, since only air and no liquid can penetrate the air filtering film and now the test strip groove is completely sealed and air pressure is increased in the sealed chamber, the liquid in liquid storage chamber cannot enter the test strip groove again.

Preferably, said connecting end of the plunger element is hermetically coupled to said piston seat through a connecting seal ring that has a circular cross section. Said working end of the plunger element is hermetically coupled to the inner wall of the opening of cup through a piston seal ring. Said piston seal ring is provided with a V-type groove of which the opening directs the bottom of the cup body. When the lid is screwed to the cup, the plunger element is hermetically coupled to the lid. The working end of the plunger element is hermetically coupled to the inner wall of the opening to insulate the liquid storage chamber from the outer atmosphere. While the lid continuously engages with the opening, the air inside the liquid storage chamber is compressed so that the air pressure of the liquid storage chamber is more than the outer atmosphere. Since the V-type groove of piston seal ring locates inside the liquid storage chamber while another side communicates with the atmosphere, the position of V-type groove of piston seal ring is pressed by the compressed air in the liquid storage chamber so that the opening of V-type groove of piston seal ring becomes larger and thus the piston seal ring fits the plunger element and the inner wall of opening of cup more tightly, embodying a better sealing effect.

Preferably, said lid is provided with a groove in the exterior of liquid-taking port I, and said silicon sheet I corresponds with the disc form of liquid-taking port I containing a central extrusion or convex. The silicon sheet I can be inserted in the top of lid and be aligned with the surface of lid, giving a beautiful appearance of cup lid.

Preferably, said lid is provided with a piston mounting port of which the diameter is the same as that of inner wall of piston seat. Said connecting end of piston penetrates the piston mounting port and a part of said connecting end locates in the exterior of lid. Said connecting end is hermetically coupled to said piston seat through a connecting seal ring. Said piston is provided at the connecting end with a liquid-taking port II that communicates with the liquid storage chamber. Said liquid-taking port II is provided with a silicon sheet II. Said piston is provided at the connecting end with a tear strip outside the lid. Said working end of the piston is provided with a barb and the inner wall of piston seat is provided with a clasp corresponding to the barb. Since the tear strip fixes the piston onto the lid. When being pushed, the piston is blocked by the tear strip and cannot enter into the liquid storage chamber in the cup. To begin using the cup, one needs to tear the tear strip firstly and then push the piston. The structure of such lid does not compress the air in the liquid storage chamber. Only after collecting liquid sample, can an operator press the connecting end of piston to operate test. After the piston is pushed into the liquid storage chamber of the cup, the barb will be coupled with the clasp so that the piston can hardly escape from the lid. When the quantity of technician is not enough, the operator can personally test the samples by using the detecting device one by one. The structure of liquid-taking hole II can also meet the need of opening silicon sheet II and take out a part of the liquid sample upon the completion of detecting liquid sample for other purposes, so as to avoid the trouble of repeated sampling in the field, thus greatly reducing the labor intensity and improving work efficiency.

Preferably, said cup body is provided below its opening with a flange that contains several deltoid or trapeziform pawls. The inner side of the bottom of said lid is provided with locking teeth to correspond to the pawls. When the lid is screwed towards the direction of tightening, the locking teeth of a lid will press the pawls to the state of elastic deformation. When the pawls enter the other side of locking teeth during further tightening, the elastic deformation will disappear and the pawls will restore their original state, so that the pawls will be locked by the locking teeth, thus the lid and cup form an integral body without any loosening and prevent the lid from re-opening or liquid sample from substituting by anybody else or mixing other compositions. Therefore, using this detecting device can help keeping the fairness of competitive sports.

Preferably, said base is a form of disc and its edge and cup bottom is hermetically coupled into one body through a base seal ring. After coupling with the cup, the base will close the liquid discharge chamber. The prior size of the base can just seal the hole and the position of test strips so that the space of the liquid discharge chamber is small and even in the event of large pressure difference, and the liquid discharge quantity is still limited. After thus modified, the volume of liquid discharge chamber is increased to accommodate more liquid samples. Hence, the liquid passing test strip plate will be increased to improve test precision.

Preferably, said base is provided with an arc diversion trench. The upper end of the arc diversion trench locates under the small hole, and the lower end of the arc diversion trench is provided with a flow baffle. The lower end of arc diversion trench communicates with a splitter box. The splitter box contains a front fender and a rear fender hermetically coupled in a head-to-tail way. The rear fender is higher than the flow baffle. When the liquid storage chamber begins to collect liquid sample, liquid sample maybe drops a few drops through the hole into the diversion trench under the role of gravity. Now the flow baffle can block the liquid sample dropped through the hole from entering into the splitter box before testing. The flow baffle in the lower end of diversion trench can also buffer the liquid that fast flows from the diversion trench to prevent the test strips in the slot of test strip plate from impacting of liquid that flows too fast and impairing.

Preferably, the hole in the bottom of said liquid storage chamber communicates with a longitudinally mounted liquid guide pipe. The lower end of liquid diversion pipe is 2-5 mm from arc diversion trench. When the liquid storage chamber is inverted, the lower end of liquid diversion pipe is upwards and higher than liquid level in the test groove so that the liquid in the test strip groove will not enter into the liquid storage chamber to avoid pollution to the liquid in the liquid storage chamber.

Preferably, said front fender is higher than said rear fender. In the course of a test, a liquid sample may flow from the splitter box and such configuration can lead the liquid to the empty place in the liquid discharge chamber to enable all the liquid sample flowed into the liquid discharge chamber to contact a test strip plate.

Preferably, said hole is provided with a check valve. The check valve only allows the liquid to flow from a liquid storage chamber into a test strip groove, and back flow will never occur.

Preferably, the opening of said slot of the test strip plate is provided with a sealing layer that helps to prevent the liquid from flowing out. If the cup accepts considerable impact, the liquid may overflow from the slot of the test strip plate. Said sealing layer can prevent the liquid from flowing out. The sealing layer is made of water-proof puncturable material. During the test, the test strip plate can easily puncture the sealing layer and extend its end in the liquid.

Preferably, said slot of test strip plate is inserted with a test strip plate of which the end penetrates the sealing layer. As the end of test strip plate penetrates the sealing layer, the test strips on the test strip plate can be used for testing the liquid sample.

Preferably, said slot of test strip plate is ⅕ to ⅓ as high as the cup body. The height of slot can meet the needs of a test under the circumstances of a liquid sample of less quantity.

Preferably, said test strip plate is provided with several test strip grooves. One end of the test strip groove locates at the end of test strip plate. The end of test strip plate is provided with a fender bracket surrounding the ends of test strip plate and test strip groove. Outside the test strip groove is provided with a complete or partial transparent protective sleeve. Test strips are provided in the test strip groove. On the one hand, the fender bracket can safeguard the test strips. On the other hand, when the test strip plate is inserted in the slot of the test strip plate, the fender bracket is easier to penetrate the sealing layer. The role of protective sleeve lies in the protection of test strip plate and the test strips in it. Though all or part of the protective sleeve is transparent, the protective sleeve will not affect the color change of test strips.

Preferably, said opening in the upper part of cup body is provided with a bulge loop below the external thread. The bulge loop is provided with one or several wedge-shaped bulges that correspond to the wedge-shaped bulges below the lower part of sealing lid respectively. The wedge-shaped bulges have high surfaces, low surfaces and bevels. In the course of screwing along sealing lid, bevels contact firstly between wedge-shaped bulges, after the transition of elastic deformation of both bulges, the high surfaces of corresponding bulges will contact. Now due to the obstruction of bulged extrusion, unless physically damaged, the bulges cannot conversely rotate, thus playing an important role in guaranteeing the fairness of competitive sports.

Therefore, the present invention is characterized by its simple operation, airtight and irreversible sealing, less influence by surrounding environment, improved safety for operators and less requirement for the quantity of liquid samples. The interior of the device only comprises two chambers of which one chamber only communicates with the other chamber for collecting and storing liquid sample. Before testing, the liquid in the liquid storage chamber holds still only by means of liquid tension and the air pressure in said chamber. Only when the plunger element attached in cup lid press the air in the liquid storage chamber can the test begin. Compared with prior device of detecting liquid sample, the present invention is characterized by its simpler structure, more convenient processing and assembling, more reasonable working mode, more pressure difference, a large volume of testing chamber than that in prior art, and an increased liquid discharge quantity under increased pressure difference to avoid the fact that test cannot be operated due to less liquid charging. Meanwhile, the air filtering hole enables the liquid quantity in test strip groove to get more precise control.

DETAILED DESCRIPTION OF THE PREFERRED EMBODIMENTS

The above and other objects, features and advantages of the present invention will be more clearly understood from the following detailed embodiments taken in conjunction with the accompanying drawings.

Example 1

Figure 1:
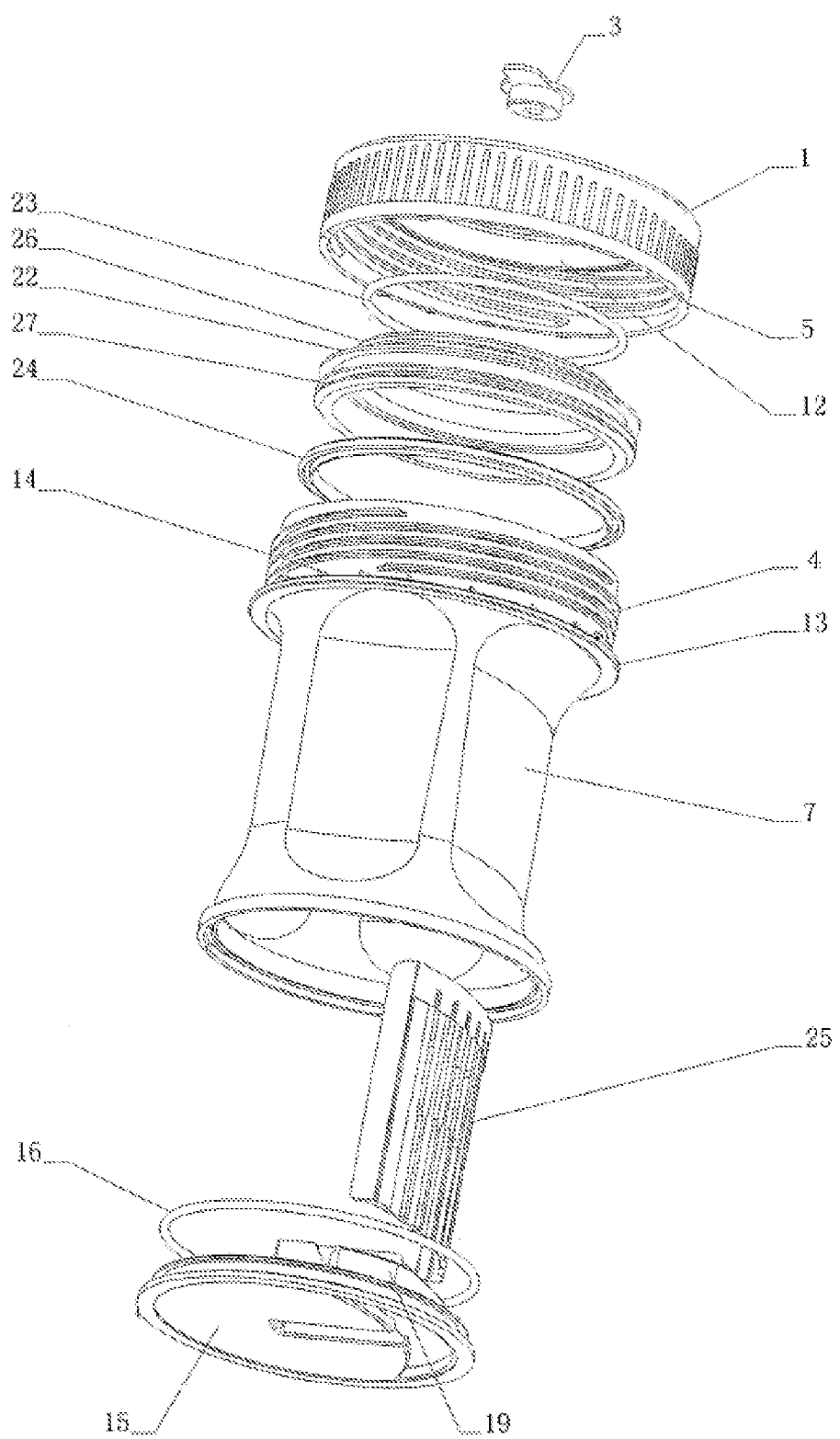
FIG. 1 is a schematic view of assembled structure according to the present invention.
Figure 2:
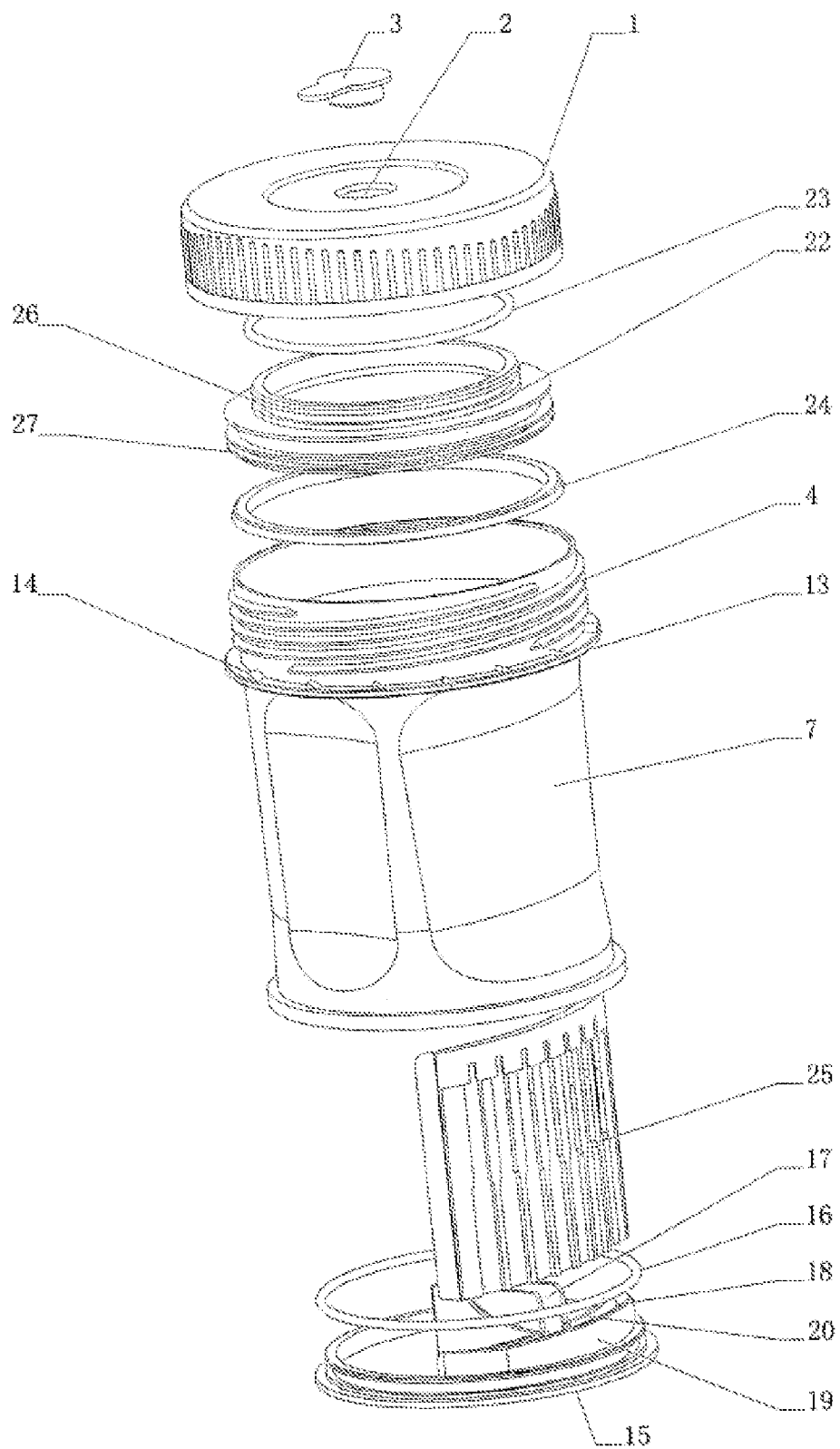
FIG. 2 is another schematic view of assembled structure according to the present invention.
Figure 3:
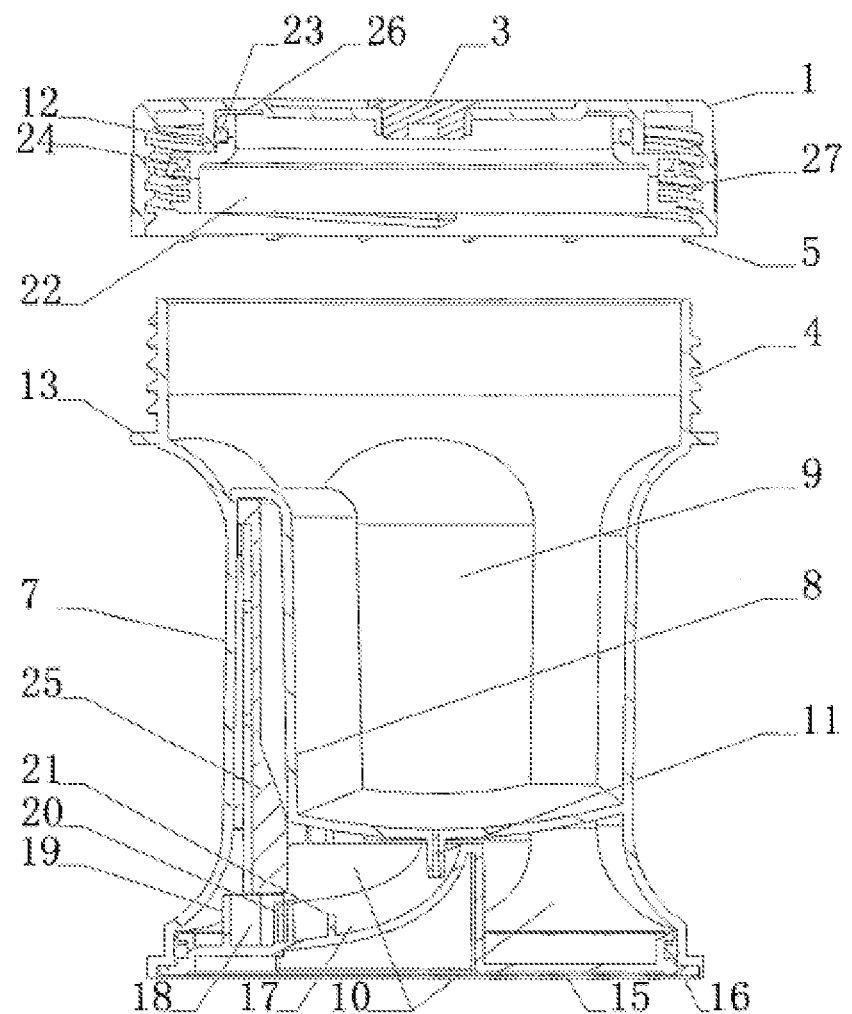
FIG. 3 is another schematic view of assembled structure according to the present invention.
Figure 4:
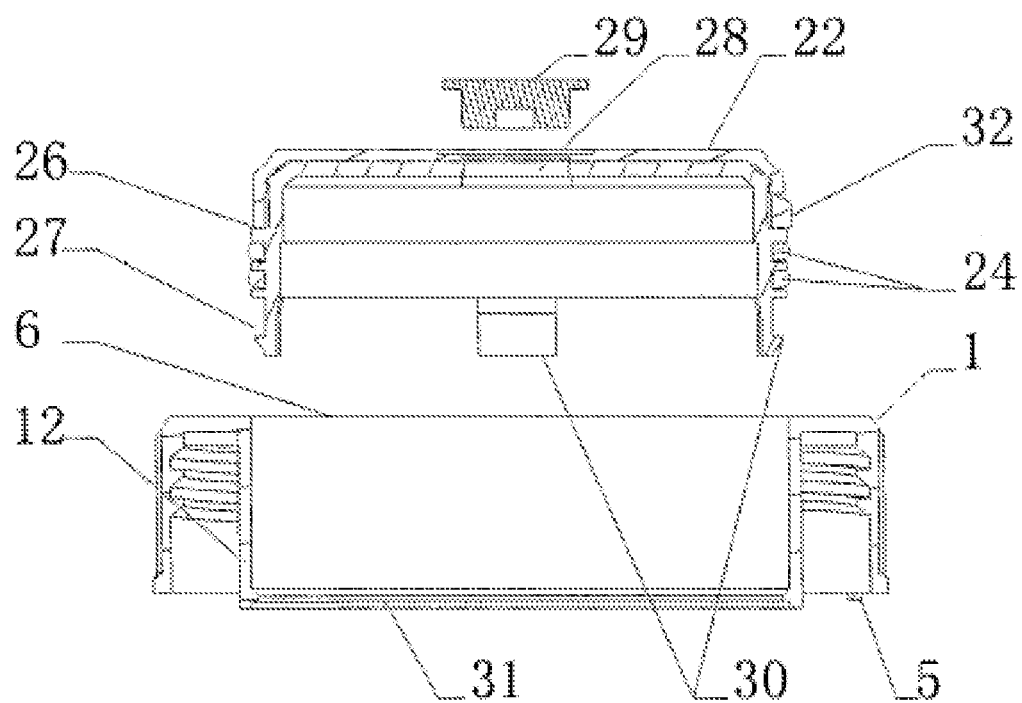
FIG. 4 is a schematic view of assembled structure of lid according to the present invention.
Figure 5:
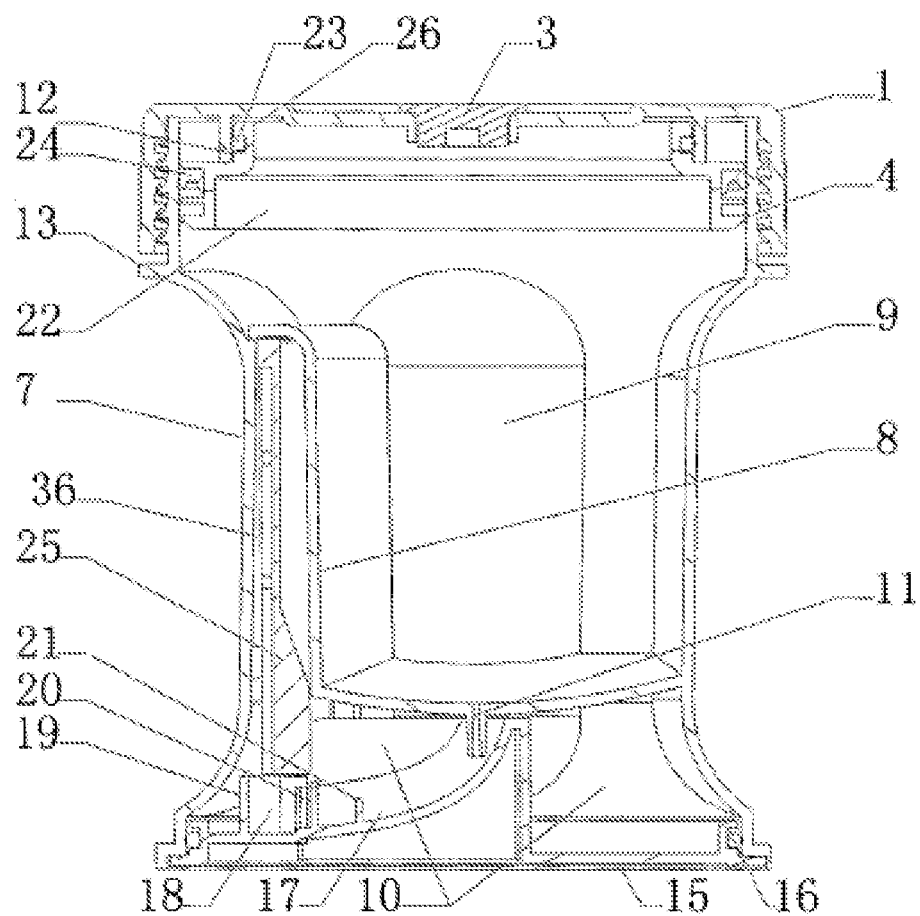
FIG. 5 is another schematic view of assembled structure according to the present invention.

The first Example of the present invention is shown in FIG. 1 and FIG. 2. The device for detecting analytes in fluid samples comprises a lid 1, a cup body 7, a test strip plate 25 and a base 15. Inside the lid 1 is provided a plunger element 22 that is hermetically coupled to the lid 1 by a circular piston seat 12 inside the lid 1. The plunger element 22, also in circular form, has a zigzag cross section (Z-shape), a connecting end 26 and a working end 27 as shown in FIG. 3 and FIG. 5. The outer diameter of connecting end 26 is less than that of working end 27. Meanwhile the outer diameter of connecting end 26 is less than that of inner diameter of piston seat 12. The connecting end 26 is hermetically coupled to the inside of piston seat 12 by a connecting seal ring 23 that has a circular cross section. As shown in FIG. 4, the lid 1 is provided with a liquid-taking port I2 communicating with the area where the plunger element 12 lies in. The lid 1 is provided with a groove in the outside of liquid-taking port I2 of which the cross section is in T type. A silicon sheet I3 in the same shape as the liquid-taking port I2 is provided on the liquid-taking port I2. The silicon sheet I3 corresponds to the disc shape of the liquid-taking port I2 with a central extrusion of a diameter slightly greater than the minimum diameter of the liquid-taking port I2, thus the silicon sheet I3 after its elastic deformation will form a hermetical coupling with the lid 1.

As shown in FIGS. 1, 2, 3 and 5, the cup body 7 is made of transparent material with a screw-thread opening 4 at its upper part. A circular flange 13 is provided beneath the opening 4. The cup body includes a liquid storage chamber and a testing trench, wherein the testing trench is located on one side of the liquid storage chamber and in communication with the liquid storage chamber through a hole at the bottom of the liquid storage chamber. The testing trench matches with a testing plate, wherein the cup lid and cup opening fit each other hermetically; the cup opening directly communicates with the liquid storage chamber. The testing trench and the bottom base form a hermetically sealed chamber. The testing trench is comprised of a testing plate trench/slot 36 and a testing liquid discharge chamber 10. The testing liquid chamber trench and the testing plate match with each other. The testing liquid discharge chamber is located below the liquid storage chamber and in direct connection with the testing plate slot and in connection with the liquid storage chamber through a small hole at the bottom of the liquid storage chamber. The volume of the part in leveling form above the baffle plate 8 is less than the volume of the part in leveling form below the baffle plate 8, thus the central vertical part is near the cup body 7 and the liquid discharge chamber 10 is like L type. A piece of paper to detect sample is provided on the test strip plate 25 installed in the liquid discharge chamber 10 in a place of the least distance between the baffle plate 8 and the cup body 7. The curve bottom of the baffle plate 8 is in a form of upside-down arch and its cross section is in an arch curve form. The bottom of baffle plate 8 is provided with a small through hole 11 and an integral part extending downwards from the edge of hole 11. The liquid storage chamber 9 directly communicates with the liquid discharge chamber 10 through the small hole 11. An opening 4 can be screwed tightly with the lid 1. A working end 27 of the plunger element 22 is provided with a piston seal ring 24 with a V-shape groove. Thus the cross section of piston seal ring 24 is in V-shape. The working end 27 is hermetically coupled to the inside cup wall of the opening 4 by the piston seal ring 24 of which the V-type groove opening faces the bottom of the cup body 7, thus lid 1 screwed on opening 4 forms a piston mechanism. The flange 13 of the cup body 7 is provided with trapeziform pawls 14 in a circular distribution, while the same distribution of locking teeth 5 corresponding to the pawls 14 is provided in an inner side of bottom of the lid 1. When the lid 1 is screwed into the cup body 7 along the opening 4, the lower end of plunger element 22 will be hermetically coupled to the cup body 7, so that the lid 1 will close the liquid storage chamber 9. Finally, one can screw the lid 1 until the pawls 14 are engaged with the locking teeth 5 so that lid 1 cannot be separated from the cup body 7. Meanwhile downwards moving lid 1 pushes the plunger element 22 to move downwards so as to gradually reduce the space in the liquid storage chamber 9 and press air as to increase the pressure that forces a part of liquid sample in the liquid storage chamber to enter into the liquid discharge chamber 10 through the small hole 11.

As shown in FIGS. 1, 2, 3 and 5, the base 15 is in the form of a disc and its edge is hermetically coupled to the bottom of the cup body 7 by a base seal ring 16. After coupling, ultrasonic welding is applied so that the liquid discharge chamber 10 can only be communicated with the liquid storage chamber 9 through the small hole 11 and cannot be communicated with any place else. The base 15 is provided with an arc diversion trench 17 in its upper part on the side of the liquid discharge chamber 10. The top of the diversion trench 17 is right under the hole 11 so that the downward extending part of the baffle plate 8 extends into the diversion trench 17. The base 15 is also provided with a splitter box 18 that locates below the liquid discharge chamber 10 to install a test strip plate 25. The bottom of the test strip plate 25 is inserted into the splitter box 18 so that the test strip plate 25 is vertically placed in the interior of the cup body 7. A splitter box 18 comprises a higher front fender 19 and a lower rear fender 20 hermetically coupled with each other. The lower end of the diversion trench 17 is coupled to s rear fender 20 of the splitter box 18 and communicated with the splitter box 18. The lower end of the diversion trench 17 is provided with a flow baffle 21 that is lower than rear fender 20.

During tests, the lid 1 is firstly removed from the opening of the cup and a liquid sample is collected from the opening 4 into the cup body 7. Then, the liquid in the cup body 7 begins to be collected in the liquid storage chamber 9 through the hole 11 under the action of baffle plate 8. Because the hole 11 is so small that the liquid, under the effects of surface tension of the liquid and the air pressure inside the liquid discharge chamber 10 simultaneously, the liquid cannot enter into the liquid discharge chamber 10 through the small hole 11. The liquid sample is in a stationary state. Then, the lid 1 is screwed onto the opening of the cup body 7. Now the plunger element 22 inside the lid 1 is hermetically coupled to the cup body 7 by a piston seal ring 24. With the downward movement of the screwing lid 1, the volume of air in the liquid storage chamber 9 defined by the plunger element 22 in the lid 1 and cup body 7 is reduced. The downward movement of lid 1 brings the plunger element 22 to move downward and further to compress the air inside the liquid storage chamber 9 continuously. Meanwhile, the liquid discharge chamber 10, after the liquid sample in the liquid storage chamber closes the small hole 11, forms an airtight space. Since the pressure is increasing gradually inside the liquid storage chamber 9, a pressure difference occurs between the liquid storage chamber 9 and the liquid discharge chamber 10. When the pressure difference breaks the original balance of the liquid sample, a part of the liquid sample is forced to enter into the liquid discharge chamber 10 through the hole 11. The liquid thus entered flows to the splitter box 18 under the action of the diversion trench 17. The liquid thus entered has a fast flow rate. Now, the flow baffle 21 in the lower end of splitter box 18 plays a role of buffering the liquid, so that the liquid slowly enters the splitter box 18 from the lower end of the diversion trench 17 to avoid the damage caused by the liquid of too fast flow rate. After flowing into the splitter box 18, the liquid sample makes contact with the test paper on the test strip plate 25 in the splitter box. The liquid sample is absorbed by the test paper and the test result is displayed on the test paper. The liquid thus entered is then overflowed and naturally flow to the base 15 in the direction of rear fender 20 to guarantee filling adequate liquid sample into the liquid discharge chamber 10.

Compared with prior art, this invention saves an individual chamber for the action of plunger element 22 and combines the working space of plunger 22 with the space to collect the liquid sample, and tremendously simplifies the structure of the detecting device and reduces the production cost by sealing the chamber to test liquid and communicating it with the chamber to collect the liquid sample. After the device for detecting analytes in fluid samples is covered by its lid, the liquid storage chamber 9 and the liquid discharge chamber 10 jointly form an airtight space. With the later shrinkage of the volume of liquid storage chamber 9, i.e. the space to collect liquid is reduced, the whole inner space of cup body 7 is consequently reduced, so that the pressure between the liquid storage chamber 9 and the liquid discharge chamber 10 completely acts on the process of filling the liquid sample to produce greater pressure difference and higher efficiency than prior art. After test, an operator can open silicon sheet I3 and take some tested liquid sample through the liquid-taking port I2 for other purposes.

Example 2

Figure 6:
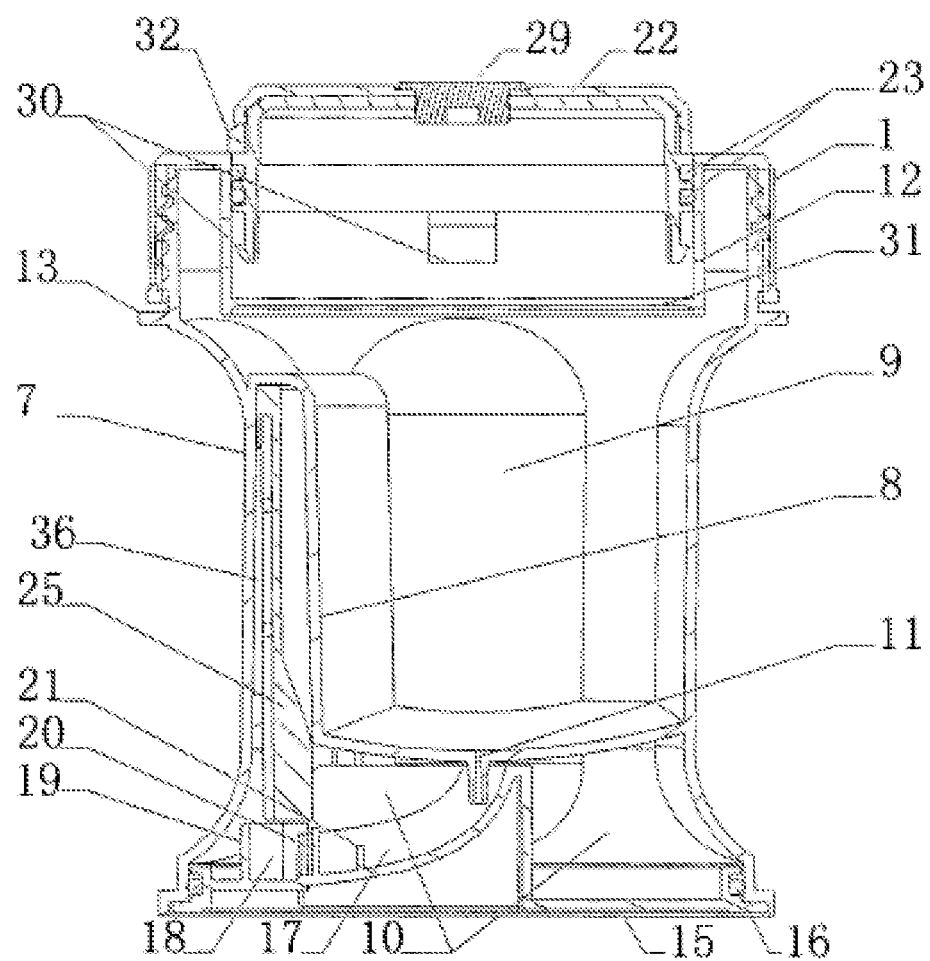
FIG. 6 is another schematic view of assembled structure according to the present invention.

FIG. 4 is a schematic view of an assembled structure of the lid according to the present invention. FIG. 6 is a schematic view of an assembled structure according to the present invention. The structures of the cup body 7, the base 15 and the test strip plate 25 are all the same as Example 1 except that the lid 1 is provided with a piston-mounting port 6. As shown in FIG. 4 and FIG. 6, the piston-mounting port 6 has the same diameter as that of an interior of piston seat 12. After mounting to a piston 22, place connecting end 26 in piston-mounting port 6 in the outside of the lid 1. A connecting end 26 is hermetically coupled to the interior of the piston seat 12 by two longitudinally mounted connecting seal rings 23 that has a circular cross section. The piston 22 is provided with a tear strip 32 at the connecting end 26 in the exterior of the lid 1.

A tear strip 32 is fixedly connected with the piston 22 and increases the perimetric size of the piston 22 so that the piston 22 is supported on the lid 1 by the tear strip 32. A working end 27 is provided with four barbs 30 that are circularly distributed, and the inner wall of a piston seat 12 is provided with clasps 31 corresponding to the barbs 30. Clasps 31 protrude towards the center of the piston seat 12. During operation, a liquid sample is firstly collected and the lid is closed.

The liquid sample in the hole 11 keeps balanced under the action of its own surface tension and air pressure inside liquid discharge chamber 10 and in a stationary state. After collecting liquid sample, one can push the piston 22 to move into the liquid storage chamber in the cup body 7 by tearing the strip 32 and pressing the part of the piston 22 protruding on the surface of the lid 1. Then the air in liquid storage chamber 9 is compressed and the pressure difference between liquid storage chamber 9 and liquid discharge chamber 10 is gradually increased, finally enabling the liquid sample to fill into the liquid discharge chamber 10 through the small hole. The barbs 30 of the piston 22 in the working end 26 are finally engaged with the clasps 31 to remove the piston from the lid. The piston 22 is provided with a liquid-taking hole II28 at a connecting end 26. The liquid-taking hole II28 communicating with the liquid storage chamber 9 has a silicon sheet II29 on it. After test, one can the open silicon sheet II29 and take the liquid sample tested through the detecting device for other purposes, like confirmation test.

Thus the storing and test of liquid sample can be separated. The process of the test is flexible. Even if technical personnel in the field are inadequate, the test process of each sample can also be observed and supervised by technical personnel, thus providing a better environment for detecting the liquid sample and more valuable test results.

Example 3

Figure 7:
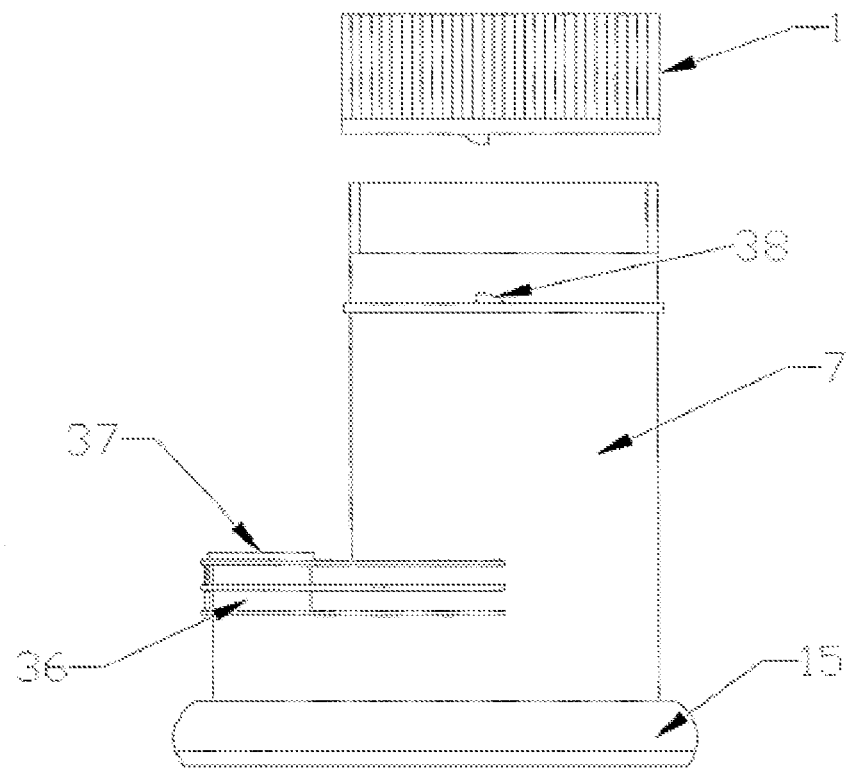
FIG. 7 is another schematic view of assembled structure according to the present invention.
Figure 8:
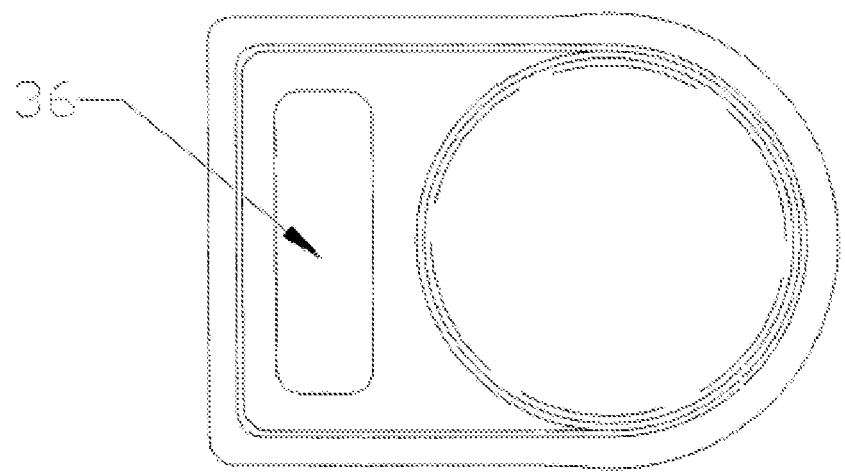
FIG. 8 is another schematic view of assembled structure according to the present invention.
Figure 9:
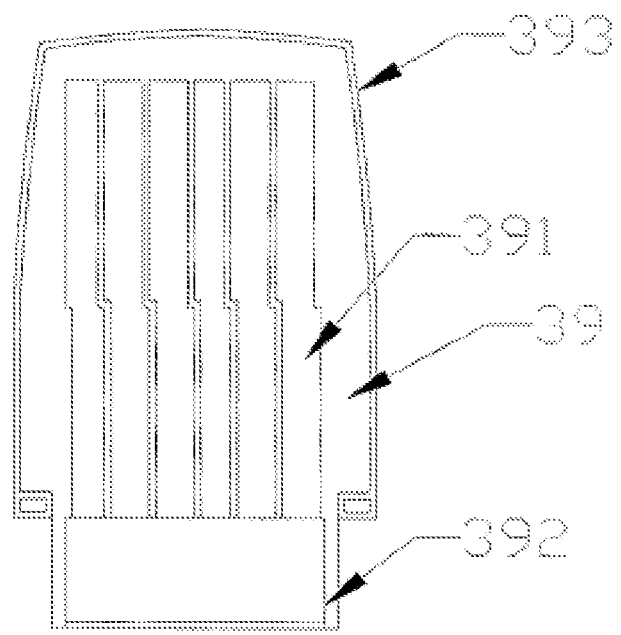
FIG. 9 is a schematic view of assembled structure of test strip plate according to the present invention.

FIG. 7 and FIG. 8 are schematic views of an assembled structure respectively according to the present invention, and FIG. 9 is a schematic view of an assembled structure of a test strip plate according to the present invention. The Example 3 contains cup body 7 with a sealing lid 1 on its tip by thread connection. The cup body and sealing lid are coupled with thread. The cup is provided with a bulge loop below the thread and the bulge loop is provided with two wedge-shaped bulges 38 while there are two wedge-shaped bulges corresponding to the above-mentioned wedge-shaped bulges respectively below the seal lid but with opposite directions of the wedge-shaped bulges' high surfaces. The cup body is provided with a testing plate slot 36 in the test strip plate at ¼ height at one side. The slot communicates with the cup body. The slot is provided with a sealing layer to separate inner space with the outside. The bottom of cup body is closely coupled with a base 6. The mouth of the slot in the test strip plate is provided with a sealing plug 3 to match the mouth of the slot. The bottom of sealing plug fits the sealing layer completely. The opening of the test strip plate slot can also be coupled with the test strip plate 39 that matches with the slot. The test strip plate is provided with six test strip grooves 391 of which front and rear ends form a curve and are not aligned in a straight line. One end of test strip groove is at the end of test strip plate that is provided with a fender bracket 392 to surround the test strip plate and the ends of test strip groove. The test strip plate is also provided with an outside clear or semi-clear protective sleeve 393. Test strips are placed in the said test strip groove.

Operation by the present invention is divided into two phases: sampling and testing. During sampling, the seal lid is opened and the sealing plug is plugged, then sample is filled and the seal lid is closed tightly with the high surfaces of corresponding wedge-shaped bulge fitting mutually by elastic deformation. Now, the seal lid cannot be opened by retrograde rotation unless physically impaired. During testing, the sealing plug is removed from the opening of test strip plate slot, exposing the sealing layer, the end of test strip plate with test strips is inserted in the slot of the test strip plate, then test strip plate penetrates the sealing layer by the fender bracket and allows the test strips to dip in the liquid sample. After the color of test strips becomes stable, test strip plate is removed and the masses and their quantity are determined contained in the liquid sample by color change.

Example 4

Figure 10:
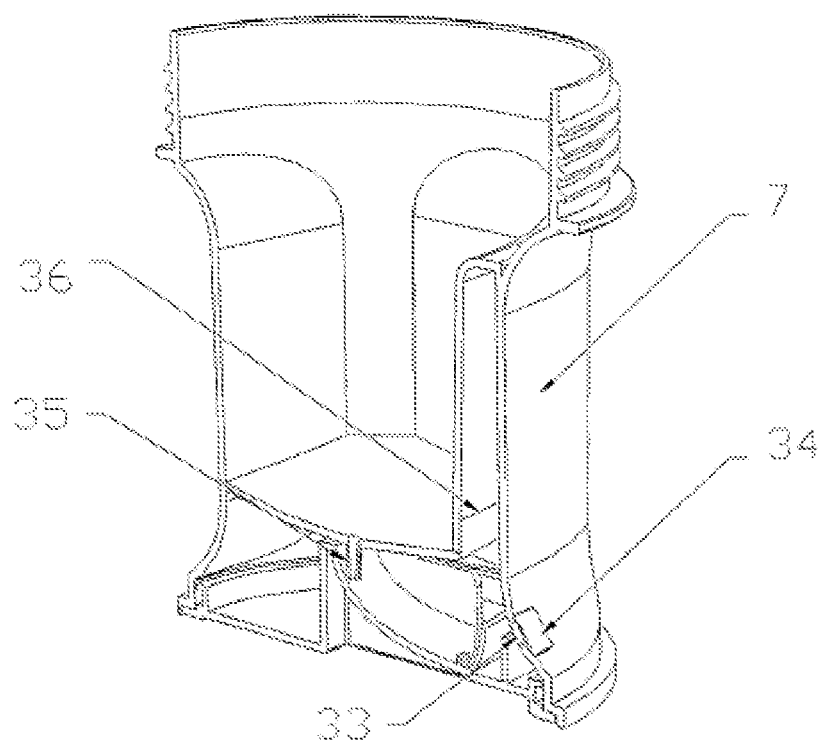
FIG. 10 is another schematic view of assembled structure according to the present invention.

Under the circumstances of Example 1 or 2, as shown in FIG. 10, the small hole in the bottom of said liquid storage chamber communicates with a vertically installed liquid guide pipe 35. The lower end of liquid diversion pipe is 2-5 mm from an arc diversion trench. The side wall of said test strip plate is provided with an air filtering hole 33 communicating with the outer atmosphere. The air filtering hole is covered by an air filtering film 34 that separates the inside and outside. When the liquid storage chamber or the whole cup body is inverted, the lower end of the liquid diversion pipe is upwards and higher than liquid level so that the liquid in test strip groove will not enter the liquid storage groove to avoid pollution to the liquid in the groove. When the liquid does not reach the height of air filtering hole, the liquid can go from the liquid storage groove to the test strip groove continuously due to the principle of communicating vessel. When the liquid level in test strip groove is higher than the air filtering hole, since only air and no liquid can penetrate the air filtering film and now the test strip groove is completely sealed and air pressure is increased, the liquid in liquid storage chamber cannot enter the test strip groove again.

Example 5

Figure 11:
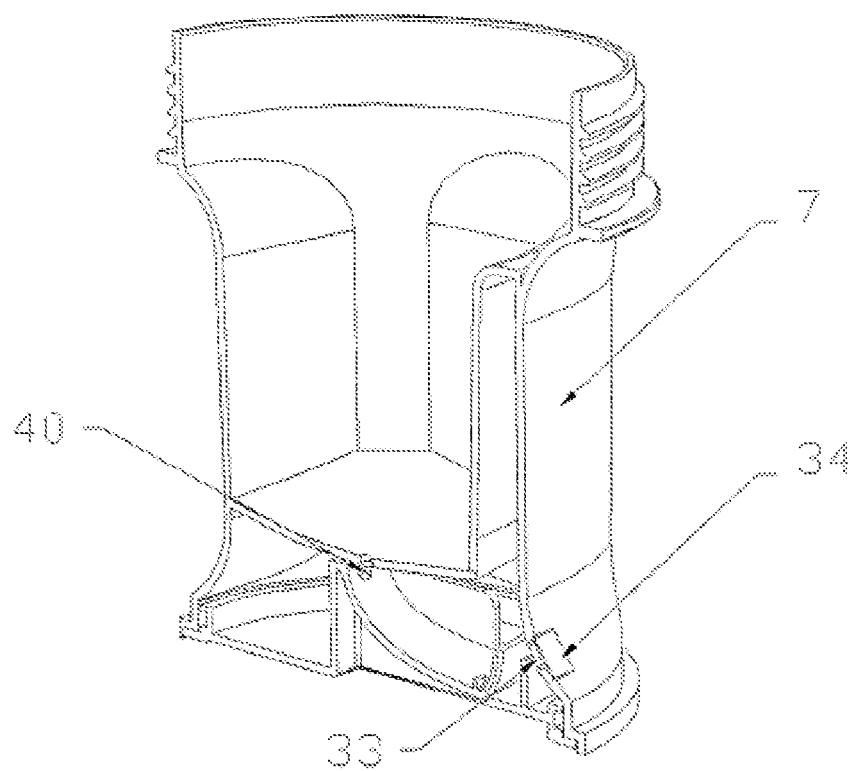
FIG. 11 is still another schematic view of assembled structure according to the present invention.

Under the circumstances of Example 1 or 2, as shown in FIG. 11, the small hole 11 includes a one-way valve 40. The valve lets liquid flow from the liquid storage chamber to the testing plate slot, but not the reverse direction, to avoid the contamination of the liquid in the liquid storage chamber. The side wall of said test strip plate is provided with an air filtering hole 33 communicating with the outer atmosphere. The air filtering hole is covered by an air filtering film 34 that separates the inside and outside to avoid the contamination of the liquid in the liquid storage chamber. When the liquid does not reach the height of air filtering hole, the liquid can go from the liquid storage groove to the test strip groove continuously due to the principle of communicating vessel. When the liquid level in the test strip groove is higher than the air filtering hole, since only air and no liquid can penetrate the air filtering film and now the test strip groove is completely sealed and air pressure is increased, the liquid in liquid storage chamber cannot enter the test strip groove again.

Therefore, the present invention is rational in structure and convenient in operation, and has solved the following problems in prior art: inadequate seal, reopening after seal, easily contamination to operators, and difficulties in tests for samples of less quantity. The precise detection of sample is of great importance to the precise judgment of criminal investigation and fairness in competitive sports.

The invention claimed is:
1. A device for detecting analytes in a liquid sample, comprising:
    a cup body;
    a lid; and
    a base;
    wherein the cup body comprises a liquid storage chamber and a test strip groove; the test strip groove locates in one side of the liquid storage chamber and communicates with the liquid storage chamber through a small hole; the test strip groove is configured to match with a test strip plate, the lid being able to seal an opening of the cup tightly, the opening of cup being directly connected with the liquid storage chamber; and
    wherein the test strip groove and the base jointly form a sealed chamber, the test groove being comprised of a test strip plate slot and a liquid discharge chamber, a side wall of the test strip plate slot is provided with an air filtering hole communicating with the atmosphere and the air filtering hole is covered by an air filtering film to allow only air to penetrate the air filtering film.

2. The device for detecting analytes in fluid samples according to claim 1, wherein a plunger element is attached in the lid, when a lid is applied onto the opening of the cup, the plunger element increases the air pressure in the liquid storage chamber so that the increased air pressure force a part of liquid sample enter into the test strip grove.

3. The device for detecting analytes in fluid samples according to claim 1, wherein the test strip plate slot matching with the test strip plate, the liquid discharge chamber being provided in a lower part of the liquid discharge chamber directly communicating with the test strip plate slot and, through a hole in a bottom of the liquid discharge chamber, communicating with the liquid discharge chamber, the lid being provided with a piston seat, the piston seat being provided with a plunger element, the plunger element being provided with a connecting end and a working end, the connecting end matching with the piston seat while the working end matching with an inner wall of an opening of the cup body.

4. The device for detecting analytes in fluid samples according to claim 3, wherein the connecting end is hermetically coupled to the piston seat by connecting a seal ring that has a circular cross section, the working end is hermetically coupled to the inner wall of opening by a piston seal ring, the piston seal ring is provided with a V-shaped groove of which the opening directs the bottom of the cup body.

5. The device for detecting analytes in fluid samples according to claim 3, wherein the lid is provided with a groove outside of a liquid-taking port I and the silicon sheet I corresponds to disc shape of the liquid-taking port I with a central extrusion.

6. The device for detecting analytes in fluid samples according to claim 3, wherein the lid is provided with a piston mounting port whose diameter is the same as that of an inner wall of the piston seat, the connecting end of the plunger element penetrates the piston mounting port and a part of the connecting end locates in an exterior of lid, the connecting end is hermetically coupled to the piston seat by a connecting seal ring, the plunger element is provided at the connecting end with a liquid-taking port II that communicates with the liquid storage chamber, the liquid-taking port II is provided with a silicon sheet II, the piston is provided at the connecting end with a tear strip outside the lid, the working end is provided with a barb and the inner wall of the piston seat is provided with a clasp corresponding the barb.

7. The device for detecting analytes in fluid samples according to claim 3, wherein the cup body is provided below its opening with a flange that contains a plurality of deltoidal or trapeziform pawls, and an inner side of a bottom of the lid is provided with locking teeth to correspond to the deltoidal or trapeziform pawls.

8. The device for detecting analytes in fluid samples according to claim 3, wherein the base is a form of a disc and edge of the disc and a bottom of the cup is hermetically coupled into one body through a base seal ring.

9. The device for detecting analytes in fluid samples according to claim 3, wherein the base is provided with an arc diversion trench of which an upper end locates under the hole and a lower end provided with a flow baffle communicates with a splitter box that comprises a front fender and a rear fender hermetically coupled in head-to-tail way, and the rear fender is higher than the flow baffle.

10. The device for detecting analytes in fluid samples according to claim 9, wherein the hole in the bottom of the liquid storage chamber communicates with a longitudinally mounted liquid guide pipe, and the lower end of liquid diversion pipe is 2-5 mm from arc diversion trench.

11. The device for detecting analytes in fluid samples according to claim 10, wherein the front fender is higher than the rear fender.

12. The device for detecting analytes in fluid samples according to claim 1, wherein the small hole comprises a check valve.

13. The device for detecting analytes in fluid samples according to claim 12, wherein the test strip plate slot is inserted with a test strip plate of which the end penetrates a sealing layer.

14. The device for detecting analytes in fluid samples according to claim 1, wherein an opening in an upper part of cup body is provided below an external thread with a bulge loop that has one or several wedge-shaped bulges corresponding to the wedge-shaped bulges below a lower part of sealing lid respectively.

\* \* \* \* \*